US008920731B2

(12) United States Patent
Nhan et al.

(10) Patent No.: US 8,920,731 B2
(45) Date of Patent: Dec. 30, 2014

(54) NONWOVEN-BASED CHEMI-CAPACITIVE OR CHEMI-RESISTIVE GAS SENSOR (75) Inventors: Davis-Dang Nhan, Appleton, WI (US); Sudhanshu Gakhar, Neenah, WI (US); Sridhar Ranganathan, Suwanee, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 309 days.

(21) Appl. No.: 12/886,238

(22) Filed: Sep. 20, 2010

(65) Prior Publication Data
US 2012/0071362 A1    Mar. 22, 2012

(51) Int. Cl.
G01N 15/06 (2006.01)
G01N 33/00 (2006.01)
G01N 33/48 (2006.01)
G01N 17/04 (2006.01)

(52) U.S. Cl.
CPC ............ *G01N 33/0047* (2013.01); *G01N 17/04* (2013.01)
USPC .................................. 422/98; 422/83; 422/88

(58) Field of Classification Search
USPC ................................................ 422/83, 88, 98
See application file for complete search history.

(56) References Cited

U.S. PATENT DOCUMENTS

| | | | |
|---|---|---|---|
| 3,045,198 A | 7/1962 | Dolan | |
| 4,129,030 A | 12/1978 | Dolan | |
| 4,224,595 A | 9/1980 | Dolan | |
| 4,237,721 A | 12/1980 | Dolan | |
| 5,114,781 A | 5/1992 | Morman | |
| 5,571,401 A | 11/1996 | Lewis | |
| 5,911,930 A * | 6/1999 | Kinlen et al. | ................ 264/104 |
| 5,951,846 A | 9/1999 | Lewis | |
| 6,085,576 A | 7/2000 | Sunshine | |
| 6,290,911 B1 | 9/2001 | Lewis | |
| 6,350,369 B1 | 2/2002 | Lewis | |
| 6,902,701 B1 | 6/2005 | Hughes | |
| 7,175,885 B2 | 2/2007 | Lewis | |
| 7,463,040 B2 * | 12/2008 | Qi et al. | ........................ 324/693 |
| 7,531,136 B2 | 5/2009 | Besnard | |
| 2002/0081397 A1 | 6/2002 | Mcgill | |
| 2005/0150778 A1 | 7/2005 | Lewis | |
| 2006/0004273 A1 * | 1/2006 | Lobodzinski | ................ 600/395 |
| 2006/0249402 A1 | 11/2006 | Snow | |

(Continued)

OTHER PUBLICATIONS

McCorkle, Dennis L. et al., "Ethanol Vapor Detection in Aqueous Environments Using Micro-Capacitors and Dielectric Polymers," Articles in Press—Sensors and Actuators, 2005, pp. 1-12.

*Primary Examiner* — Brian J Sines
(74) *Attorney, Agent, or Firm* — Denise L. Stoker; Vincent T. Kung (57) ABSTRACT

A chemical gas sensor formed from a nonwoven material is described. The gas sensor includes a flexible, gas-permeable, nonwoven web-based material substrate having a matrix that is composed of a plurality of inert thermoplastic, pulp, cellulose or staple fibers as either a major or minor portion, with a plurality of gas-sensitive fibers formed from a polymer that can absorb volatile organic compounds (VOC), and a plurality of electrically conductive fibers. The gas-sensitive fibers are intermixed with and associated spatially among a network of adjacent electrically conductive fibers, such that a change in physical morphology of said gas-sensitive fibers as a result of interacting with volatile organic compounds, causes a change in dielectric properties that disrupts said network of adjacent electrically conductive fibers. The sensor can be configured as either a resistive or a capacitive chemisensor.

9 Claims, 5 Drawing Sheets

(56) References Cited

U.S. PATENT DOCUMENTS

| | | |
|---|---|---|
| 2006/0292033 A1 | 12/2006 | Blok |
| 2007/0142799 A1 | 6/2007 | Ales |
| 2008/0150556 A1 | 6/2008 | Han et al. |
| 2008/0236251 A1* | 10/2008 | Tepper et al. ............... 73/31.05 |
| 2009/0036012 A1 | 2/2009 | Nhan et al. |
| 2009/0128168 A1* | 5/2009 | Qi et al. ..................... 324/693 |
| 2009/0321238 A1 | 12/2009 | Nhan et al. |
| 2010/0168702 A1 | 7/2010 | Ales et al. |

* cited by examiner

NONWOVEN-BASED CHEMI-CAPACITIVE OR CHEMI-RESISTIVE GAS SENSOR

FIELD OF INVENTION

The present invention pertains generally to chemical sensing devices. In particular, the invention discloses a flexible, nonwovens material-based gas sensor that can be configured in either a chemi-capacitive or chemi-resistive format.

BACKGROUND

The environment in which one lives or works in could contain hazardous chemical vapor compounds. In recent years, the gas sensor technology has advanced remarkably. Numerous kinds of gas sensors with multiple designs are available in the market for various applications ranging from industrial or manufacturing uses to consumer uses at home. However, those sensors are durable or semi-durable. A need exists for a disposable and flexible substrate that can be adapted for use with certain industrial applications and in protective gear.

SUMMARY OF THE INVENTION

In general, the present invention pertains to a chemical gas sensor. The gas sensor has a flexible, gas-permeable, nonwoven web-based material substrate having a matrix that is composed of a plurality of inert thermoplastic, pulp, cellulose or staple fibers as either a major or minor portion, as desired, with a plurality of gas-sensitive fibers formed from a polymer that can absorb volatile organic compounds (VOC), and a plurality of electrically conductive fibers. The gas-sensitive fibers are intermixed with and associated spatially among a network of adjacent electrically conductive fibers, such that a change in physical morphology of the gas-sensitive fibers, as a result of interacting with volatile organic compounds, causes a change in either physical dimensions or dielectric properties that disrupts the network of adjacent electrically conductive fibers. The flexible nonwoven matrix can be monitored for a change in relative resistivity or capacitance.

Depending on the design and desired use or method of detection, the flexible nonwoven matrix can be either a standalone layer or sheet in a resistive sensor, or situated between two conductive layers to form a capacitor. For instance, in a resistive chemisensor, the nonwoven-based material can be a single layer or sheet, which is sensitive to a relative resistivity change between about 1000 Ohms to about 10,000,000 Ohms. The nonwoven-based material can monitored for a change in relative resistivity of at least about 1000 Ohms.

Alternatively, in a capacitive chemisensor, the sensor includes a chemi-capacitive body having a first nonwoven-based electrode, a dielectric layer, and a second nonwoven-based electrode; at least one of the nonwoven-based electrodes is porous to enable gases or vapor to diffuse through said nonwoven-based material and interact with said dielectric layer. The nonwoven-based material can have a relatively wide range of capacitance, for example, sensitive to a change of about 10-100 pF.

The conductive layers can be sheets of conductive paper. The gas-sensitive fibers can be formed from one or more of various polymers that are selected to be reactive to particular VOCs. The amount of gas-sensitive fibers present in the nonwoven-based substrate can range from about 5% to about 90% by weight of the entire nonwoven matrix. The amount of electrically conductive fibers can range from about 5% or 10% or 12%, up to about 75% or 80%, depending on the total weight percentage of the remaining balance other than the gas-sensitive fibers in the entire nonwoven matrix. Other fibers that can make up the general nonwoven matrix can be selected from either natural or synthetic polymeric, cellulosic or pulp materials. In certain embodiments, the inactive thermoplastic or cellulosic web fibers can be very minimal, present in a mount of about 10%, 5%, or less (e.g., ~1-2%) of the total nonwoven material matrix; while in other embodiments, these fibers are present in more substantial amounts, for instance, up to about 50% or 60%.

A chemical array or system can include either a resistive sensor or capacitive sensor, or a combination of the two types, and various detection or reader output equipment. The electronic output device or equipment either as wired or wirelessly connected with the sensor.

An advantage of the nonwoven-based material is that the material is flexible and can be easily adapted to fit various configurations or conform to space limitations. A gas sensor constructed with the nonwoven-based material can be used, for instance, as an "end-of-life" indicator in gas masks, gas sensor badges, or moisture sensor badges, or alternatively incorporated as part of certain absorbent or protective garments or articles for various industrial or safety applications.

Other features and advantages of the present invention will be further described in the following detailed description, examples, and accompanying figures.

DETAILED DESCRIPTION OF THE INVENTION

In general, the present invention pertains to a conductive nonwoven web containing conductive fibers that may be configured as a chemical sensor. In particular, we describe a nonwoven material and a sensor containing such materials for detecting or sensing the presence of certain gases (i.e., Volatile Organic Compounds (VOC)). The nonwoven material contains at least one type of gas responsive fibers. According to embodiments, the sensor employs a nonwoven material that incorporates a multiple of different kinds of the gas responsive fibers for detecting various different VOC species. When a gas sensor according to the invention is exposed to a gas (VOC) of interest, the gas responsive fibers change their physical properties, which in turn alter the matrix or substrate of the nonwoven material. For instance, the fiber can change its dimensions (e.g., swelling or shrinking) or change its dielectric properties.

The present invention builds upon and adaptively extends the conductive nonwoven webs described in U.S. patent application Ser. Nos. 11/888,334 and 12/130,573, by Davis-Dang Nhan et al., the pertinent contents of which are incorporated herein by reference. The conductive fibers can be incorporated into the web, for instance, such that the web is electrically conductive over a zone of the nonwoven web structure. For instance, the web can be configured to that it is capable of carrying an electrical current in either length, width, or any suitable direction along the web. When the dimensions and/or dielectric properties are altered, a gas sensor with gas responsive nonwoven material can be constructed to be either a chemi-resistor or chemi-capacitor, depending on the configuration. The present invention can be used to make volatile gas sensors, such as "end of life" sensor for gas mask, gas sensor badge, moisture sensor badge.

Figure 1:
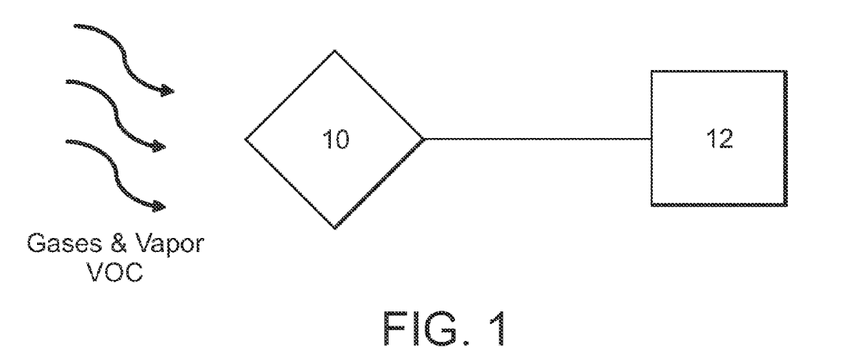
FIG. 1 shows an overview of a schematic representation of a sensor body 10—connected to a processor or reader 12.

FIG. 1 shows a general schematic representation of a gas-chemisensor according to the present invention. As illustrated in FIG. 1, gas and volatile organic compounds are taken in and react with a sensor component 10, and data or output results are delivered or transmitted to a processor or reader 12. According to the present invention, the gas-chemisensor incorporates a flexible, nonwoven-based substrate, which has a number of gas-reactive fibers distributed throughout a fiber web of the nonwoven substrate. The nonwoven material can contain at least one kind of gas-sensitive fibers, but desirably more, such as a combination of gas-sensitive fibers for different volatile gases. The gas-sensitive fibers or filaments can be made from a variety of active polymers, such as the polymer species summarized in Table I. These polymers are sensitive and reactive to the presence of a corresponding volatile organic compound (VOC).

TABLE I

Active polymers for fibers that are sensitive and reactive to corresponding volatile organic compounds (VOC)

| Polymer | Volatile Organic Compounds (VOC) |
| --- | --- |
| Poly ethylene vinyl acetate (PEVA) | Dimethyl disulfide |
| Poly vinyl alcohol (PVA) | Water vapor, alcohol vapor |
| Polyaniline | Ammonia, carbon dioxide, hydrogen sulfide, methanol, ethyl acetate, butanol, butylamine, toluene, benzene, alcohol vapor like methanol, ethanol, propanol |
| Polyepichlorohydrin | Aromatics and chlorinated hydrocarbons |
| Poly (N-vinyl pyrrolidone) | Water vapor, triethylamine, benzaldehyde, ammonia, marcaptans |

Figure 2A:
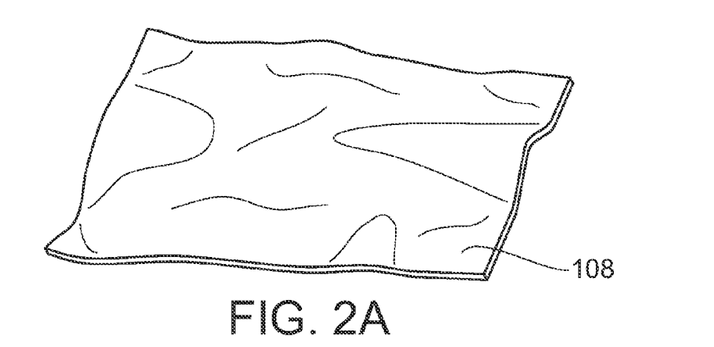
FIG. 2A is a three-quarter view of a nonwoven substrate with active or gas-respective polymer fibers distributed throughout a fiber web of the nonwoven substrate according to the present invention.
Figure 2B:
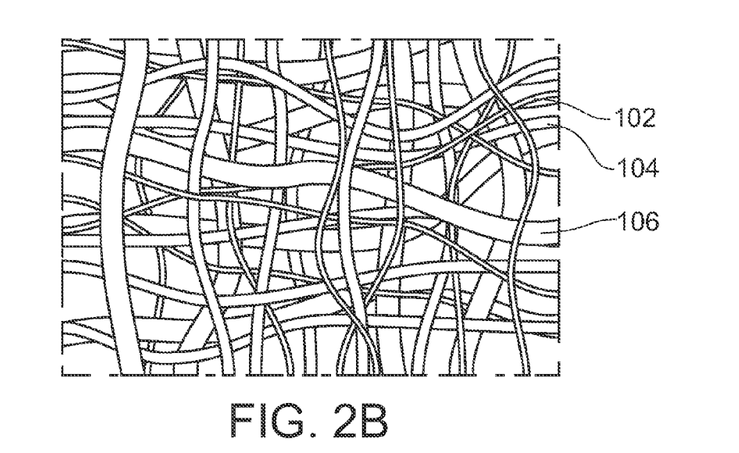
FIG. 2B is an enlarged detail of the arrangement of various gas-sensitive, active fibers 102 and electrically conductive filaments 104 on the nonwoven, and an illustration of their proximal relationship and interaction with each other.

FIG. 2A is an illustration in three-quarter view of a flexible nonwoven substrate 1 with active or gas-reactive polymer fibers 102 distributed throughout a fiber web 106 of the nonwoven material as envisioned to be placed into the sensor according to the invention. Depending on the desired uses, the gas-reactive fibers can be distributed evenly or uniformly over the surface of the nonwoven substrate or within the web or matrix of the nonwoven material; or alternatively, the active fibers can be arranged non-uniformly or concentrated at different areas of the nonwoven material, either randomly or in a pattern or design. For example, the gas reactive fibers can be either at or in certain areas of the nonwoven substrate, such as within a center region of the substrate or on the outside surface of the center region, or along peripheral regions. The fiber distribution can be either continuous or discontinuous, creating "spots" over the area of the entire nonwoven substrate in which a mix of certain areas have a higher concentration and adjacent areas have a lower concentration. The gas-reactive fibers should be distributed proximally to certain electrically conductive fibers or filaments situated within the web or matrix of the nonwoven material. In certain embodiments, the fiber mat contains conductive filaments that are uniformly distributed throughout the nonwoven material, and in other embodiments, the conductive filaments are non-uniformly distributed. Like with the gas-reactive fibers, the conductive filaments can also be either continuous or discontinuously arranged throughout the nonwoven web or on its surface. FIG. 2B shows an enlarged detail of the arrangement of the nonwoven material in FIG. 2A, showing various active gas-reactive fibers 102 and electrically conductive filaments 104 either in the web matrix, for example, of thermoplastic or cellulosic materials 106, or on surface 108 of the nonwoven material.

The flexible nature of the nonwoven material is an advantage when one desires to configure the material into a variety of shapes or sizes. For instance, one can fit a greater amount of reactive surface area material into compact or small spaces (e.g., up to about 2-5 cm in diameter or cross dimensions) than with conventional materials and designs. Practical applications for a flexible, nonwoven material-based gas sensor can be found in various industrial and consumer products. For instance, a need exists for relatively low cost, wearable, disposable gas sensors that can be used in protective respiratory products, such as an end-of-life sensor for gas mask, personal gas sensor for chemical factory workers. The nonwoven based sensor according to the invention can be configured to function by either a chemi-capacitor or chemi-resistor mode of detection.

Section I

Conductive Nonwoven-Based Substrate

The present nonwoven-based gas sensor employs conductive nonwoven materials that are similar to those described in U.S. patent application Ser. No. 12/341,419, and Ser. No. 12/474,024, the contents of which are incorporated herein by reference. In the present invention, however, in addition to conductive fibers, the nonwoven substrate also contains gas-sensitive active fibers. In particular, the nonwoven material is composed of a plurality of inert thermoplastic, pulp, cellulose or staple fibers as a major portion, with a plurality of gas-sensitive fibers formed from a polymer that can absorb volatile organic compounds (VOC), and a plurality of electrically conductive fibers. The conductive fibers can be incorporated into the web, for instance, such that the web is electrically conductive in at least one direction. For instance, the nonwoven web can be made so that it is capable of carrying an electric current in the length direction, in the width direction, or in any suitable direction. The gas-sensitive active fibers are likewise integrated in the web. One may arrange the gas-sensitive fibers to be uniformly and/or evenly distributed over the nonwoven web; or alternatively, one may arrange the gas-sensitive fibers into either more dense or less dense regions, such as clusters or clumps, according to either a predetermined pattern or randomly.

The amount of gas-sensitive fibers to be incorporated can be set according to a predetermined amount or according to certain set spatial arrangements as the particular application of the material and/or conditions the material is to be deployed may deem necessary. The gas-sensitive fibers can be present in an amount from about 5% to about 95% by weight; typically, the percentage is between about 20 wt. % or 22 wt % to about 90 wt. % or 93 wt. %, and more typically between about 40 wt. % or 50 wt. % to about 85 wt. % or 88 wt. %. Desirably the percentage of the gas-sensitive fibers present is a majority component; however, alternative beneficial ranges can be between about 30-32 wt. % or 35 wt % to about 75-83 wt. % or 85 wt. %, such as about 45 wt. % to about 80 wt. %. The remaining balance of the nonwoven material can be made up of conductive fibers or filaments and other kinds of natural or synthetic fibers or filaments, such as polymeric, cellulosic or pulp materials. The amount of these other components may range between about 5 or 10 wt. % to about 55-60-75 wt. % of the total weight depending on the embodiment. Of the remainder, it is desirable that the electrically conductive filaments constitute a major portion; for instance, between about 12%, 25% or 30% up to about 60%, 70% or 80%, depending on the total weight percentage of the remaining balance.

In accordance with the present invention, conductive nonwoven webs can contain a substantial amount of pulp fibers and can be made using a paper making process. For instance, in one embodiment, the conductive fibers can be combined with pulp fibers and water to form an aqueous suspension of fibers that is then deposited onto a porous surface for forming a conductive tissue web. The conductivity of the tissue web can be controlled by selecting particular conductive fibers, locating the fibers at particular locations within the web and by controlling various other factors and variables. In one embodiment, for instance, the conductive fibers incorporated into the nonwoven web comprise chopped carbon fibers.

After a conductive nonwoven material is made in accordance with the present disclosure, the material can be cut into a plurality of slits that are then wound onto spools. Each slit, for instance, can have a width of from about 1 mm to about 15 mm, such as from about 3 mm to about 10 mm. Once wound onto a spool, each slit can be later incorporated into any suitable product.

As described above, the base webs of the present disclosure are made by combining conductive fibers with pulp fibers to form nonwoven webs. In one embodiment, a tissue making process or a paper making process is used to form the webs.

The conductive fibers that may be used in accordance with the present disclosure can vary depending upon the particular application and the desired result. Conductive fibers that may be used to form the nonwoven webs include carbon fibers, metallic fibers, conductive polymeric fibers including fibers made from conductive polymers or polymeric fibers containing a conductive material, metal coated fibers, and mixtures thereof. Metallic fibers that may be used include, for instance, copper fibers, aluminum fibers, and the like. Polymeric fibers containing a conductive material include thermoplastic fibers coated with a conductive material or thermoplastic fibers impregnated or blended with a conductive material. For instance, in one embodiment, thermoplastic fibers may be used that are coated with silver.

The conductive fibers incorporated into the nonwoven material can have any suitable length and diameter. In one embodiment, for instance, the conductive fibers can have an aspect ratio of from about 100:1 to about 1,000:1.

The amount of conductive fibers contained in the nonwoven web can vary based on many different factors, such as the type of conductive fiber incorporated into the web and the ultimate end use of the web. The conductive fibers may be incorporated into the nonwoven web, for instance, in an amount from about 1% by weight to about 90% by weight. In particular embodiments, the conductive fibers can be present in the nonwoven web in an amount from about 5% or 7% by weight to about 25% or 30% by weight, and more typically from about 8% or 10% by weight to about 12% or 15% by weight.

Carbon fibers that may be used in the present disclosure include fibers made entirely from carbon or fibers containing carbon in amounts sufficient so that the fibers are electrically conductive. In one embodiment, for instance, carbon fibers may be used that are formed from a polyacrylonitrile (or PAN) polymer. In particular, the carbon fibers are formed by heating, oxidizing, and carbonizing polyacrylonitrile PAN polymer fibers. Such fibers typically have high purity and contain relatively high molecular weight molecules. For instance, the fibers can contain carbon in an amount greater than about 85% by weight. In one embodiment, for instance, the purity of the carbon fibers can be from about 85% to about 95%, such as from about 88% to about 92%. Although higher purity fibers have better conductive properties, the higher purity fibers can be more expensive. Sufficient electrical characteristics, on the other hand, can be obtained using fibers with the purity ranges described above.

In order to form carbon fibers from polyacrylonitrile PAN polymer fibers, the polyacrylonitrile PAN fibers are first heated in an oxygen environment, such as air. While heating, cyano sites within the polyacrylonitrile PAN polymer form repeat cyclic units of tetrahydropyridine. As heating continues, the polymer begins to oxidize. During oxidation, hydrogen is released causing carbon to form aromatic rings.

After oxidation, the fibers are then further heated in an oxygen starved environment. For instance, the fibers can be heated to a temperature of greater than about 1300° C., such as greater than 1400° C., such as from about 1300° C. to about 1800° C. During heating, the fibers undergo carbonization. During carbonization, adjacent polymer chains join together to form a lamellar, basal plane structure of nearly pure carbon.

Polyacrylonitrile-based carbon fibers are available from numerous commercial sources. For instance, such carbon fibers can be obtained from Toho Tenax America, Inc. of Rockwood, Tenn.

Other raw materials used to make carbon fibers are Rayon and petroleum pitch.

Of particular advantage, the formed carbon fibers can be chopped to any suitable length. In one embodiment of the present disclosure, for instance, chopped carbon fibers may be incorporated into the base web having a length of from about 1 mm to about 6 mm, such as from about 2 mm to about 5 mm. The fibers can have an average diameter of from about 3 microns to about 15 microns, such as from about 5 microns to about 10 microns. In one embodiment, for instance, the carbon fibers may have a length of about 3 mm and an average diameter of about 7 microns.

In one embodiment, the carbon fibers incorporated into the nonwoven base webs have a water soluble sizing. Sizing can be in the amount of 0.1-10% by weight. Water soluble sizings, can be, but not limited to, polyamide compounds, epoxy resin ester and poly(vinyl pyrrolidone). In this manner, the sizing is dissolved when mixing the carbon fibers in water to provide a good dispersion of carbon fibers in water prior to forming the nonwoven web. The sizing also assists in handling the fibers, by controlling them from becoming airborne while being added during the process.

In forming conductive nonwoven webs in accordance with the present disclosure, the above conductive fibers are combined with other fibers suitable for use in tissue or paper making processes. The fibers combined with the conductive fibers may comprise any natural or synthetic cellulosic fibers including, but not limited to nonwoody fibers, such as cotton, abaca, kenaf, sabai grass, flax, esparto grass, straw, jute hemp, bagasse, milkweed floss fibers, algae fibers, and pineapple leaf fibers; and woody or pulp fibers such as those obtained from deciduous and coniferous trees, including softwood fibers, such as northern and southern softwood kraft fibers; hardwood fibers, such as eucalyptus, maple, birch, and aspen. Pulp fibers can be prepared in high-yield or low-yield forms and can be pulped in any known method, including kraft, sulfite, high-yield pulping methods and other known pulping methods. Fibers prepared from organosolv pulping methods can also be used, including the fibers and methods disclosed in U.S. Pat. No. 4,793,898, issued Dec. 27, 1988 to Laamanen et al.; U.S. Pat. No. 4,594,130, issued Jun. 10, 1986 to Chang et al.; and U.S. Pat. No. 3,585,104. Useful fibers can also be produced by anthraquinone pulping, exemplified by U.S. Pat. No. 5,595,628 issued Jan. 21, 1997, to Gordon et al.

In one embodiment, softwood fibers are used to produce the nonwoven material. Softwood fibers tend to be longer which reduces particulate emission during manufacturing and converting. The longer pulp fibers also have a tendency to entangle better with the conductive fibers, such as the carbon fibers.

The pulp fibers incorporated into the nonwoven material, such as softwood fibers, can also be refined so as to increase the amount of bonding sites on each fiber. The increase in bonding sites increases the mechanical entanglement of the pulp fibers with the conductive fibers in the finished material. This allows for a very flat uniform paper with reduced carbon fiber fallout during processing. The refining action also increases the overall strength of the nonwoven material. For example, in one embodiment, the pulp fibers can have a Canadian Standard Freeness of greater than about 350 mL, such as greater than about 375 mL. For instance, the pulp fibers can be refined so as to have a Canadian Standard Freeness of from about 350 mL to about 600 mL.

A portion of the fibers, such as up to 50% or less by dry weight, or from about 5% to about 30% by dry weight, can be synthetic fibers such as rayon, polyolefin fibers, polyester fibers, polyvinyl alcohol fibers, bicomponent sheath-core fibers, multi-component binder fibers, and the like. An exemplary polyethylene fiber is Pulpex®, available from Hercules, Inc. (Wilmington, Del.). Synthetic cellulose fiber types include rayon in all its varieties and other fibers derived from viscose or chemically-modified cellulose.

Incorporating thermoplastic fibers into the nonwoven web may provide various advantages and benefits. For example, incorporating thermoplastic fibers into the web may allow the webs to be thermally bonded to adjacent structures. For instance, the webs may be thermally bonded to other nonwoven materials, such as a diaper liner which may comprise, for instance, a spunbond web or a meltblown web.

Chemically treated natural cellulosic fibers can also be used such as mercerized pulps, chemically stiffened or crosslinked fibers, or sulfonated fibers. For good mechanical properties in using papermaking fibers, it can be desirable that the fibers be relatively undamaged and largely unrefined or only lightly refined. Mercerized fibers, regenerated cellulosic fibers, cellulose produced by microbes, rayon, and other cellulosic material or cellulosic derivatives can be used. Suitable fibers can also include recycled fibers, virgin fibers, or mixtures thereof.

Other papermaking fibers that can be used in the present disclosure include paper broke or recycled fibers and high yield fibers. High yield pulp fibers are those papermaking fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin. High yield fibers are well known for their stiffness in both dry and wet states relative to typical chemically pulped fibers.

In general, any process capable of forming a tissue or paper web can be utilized in forming the conductive web. For example, a papermaking process of the present disclosure can utilize embossing, wet pressing, air pressing, through-air drying, uncreped through-air drying, hydroentangling, air laying, as well as other steps known in the art. The tissue web may be formed from a fiber furnish containing pulp fibers in an amount of at least 50% by weight, such as at least 60% by weight, such as at least 70% by weight, such as at least 85% by weight.

The nonwoven webs can also be pattern densified or imprinted, such as the tissue sheets disclosed in any of the following U.S. Pat. No. 4,514,345 issued on Apr. 30, 1985, to Johnson et al.; U.S. Pat. No. 4,528,239 issued on Jul. 9, 1985, to Trokhan; U.S. Pat. No. 5,098,522 issued on Mar. 24, 1992; U.S. Pat. No. 5,260,171 issued on Nov. 9, 1993, to Smurkoski et al.; U.S. Pat. No. 5,275,700 issued on Jan. 4, 1994, to Trokhan; U.S. Pat. No. 5,328,565 issued on Jul. 12, 1994, to Rasch et al.; U.S. Pat. No. 5,334,289 issued on Aug. 2, 1994, to Trokhan et al.; U.S. Pat. No. 5,431,786 issued on Jul. 11, 1995, to Rasch et al.; U.S. Pat. No. 5,496,624 issued on Mar. 5, 1996, to Steltjes, Jr. et al.; U.S. Pat. No. 5,500,277 issued on Mar. 19, 1996, to Trokhan et al.; U.S. Pat. No. 5,514,523 issued on May 7, 1996, to Trokhan et al.; U.S. Pat. No. 5,554,467 issued on Sep. 10, 1996, to Trokhan et al.; U.S. Pat. No. 5,566,724 issued on Oct. 22, 1996, to Trokhan et al.; U.S. Pat. No. 5,624,790 issued on Apr. 29, 1997, to Trokhan et al.; and, U.S. Pat. No. 5,628,876 issued on May 13, 1997, to Ayers et al., the disclosures of which are incorporated herein by reference to the extent that they are non-contradictory herewith. Such imprinted tissue sheets may have a network of densified regions that have been imprinted against a drum dryer by an imprinting fabric, and regions that are relatively less densified (e.g., "domes" in the tissue sheet) corresponding to deflection conduits in the imprinting fabric, wherein the tissue sheet superposed over the deflection conduits was deflected by an air pressure differential across the deflection conduit to form a lower-density pillow-like region or dome in the tissue sheet.

Wet and dry strength agents may be applied or incorporated into the base sheet. As used herein, "wet strength agents" refer to materials used to immobilize the bonds between fibers in the wet state. Typically, the means by which fibers are held together in paper and tissue products involve hydrogen bonds and sometimes combinations of hydrogen bonds and covalent and/or ionic bonds. In the present invention, it may be useful to provide a material that will allow bonding of fibers in such a way as to immobilize the fiber-to-fiber bond points and make them resistant to disruption in the wet state. In the present application, wet strength agents also assist in bonding the conductive fibers, such as the carbon fibers, to the rest of the fibers contained in the web. In this manner, the conductive fibers are inhibited from falling out of the web during further handling.

Any material that when added to a tissue sheet or sheet results in providing the tissue sheet with a mean wet geometric tensile strength/dry geometric tensile strength ratio in excess of about 0.1 will, for purposes of the present invention, be termed a wet strength agent. Typically these materials are termed either as permanent wet strength agents or as "temporary" wet strength agents. For the purposes of differentiating permanent wet strength agents from temporary wet strength agents, the permanent wet strength agents will be defined as those resins which, when incorporated into paper or tissue products, will provide a paper or tissue product that retains more than 50% of its original wet strength after exposure to water for a period of at least five minutes. Temporary wet strength agents are those which show 50% or less than, of their original wet strength after being saturated with water for five minutes. Both classes of wet strength agents find application in the present invention. The amount of wet strength agent added to the pulp fibers may be at least about 0.1 dry weight percent, more specifically about 0.2 dry weight percent or greater, and still more specifically from about 0.1 to about 3 dry weight percent, based on the dry weight of the fibers.

Permanent wet strength agents will typically provide a more or less long-term wet resilience to the structure of a tissue sheet. In contrast, the temporary wet strength agents will typically provide tissue sheet structures that had low density and high resilience, but would not provide a structure that had long-term resistance to exposure to water or body fluids.

The temporary wet strength agents may be cationic, non-ionic or anionic. Such compounds include PAREZ™ 631 NC and PAREZ® 725 temporary wet strength resins that are cationic glyoxylated polyacrylamide available from Cytec Industries (West Paterson, N.J.). This and similar resins are described in U.S. Pat. No. 3,556,932, issued on Jan. 19, 1971, to Coscia et al. and U.S. Pat. No. 3,556,933, issued on Jan. 19, 1971, to Williams et al. Hercobond 1366, manufactured by Hercules, Inc., located at Wilmington, Del., is another commercially available cationic glyoxylated polyacrylamide that may be used in accordance with the present invention. Additional examples of temporary wet strength agents include dialdehyde starches such as Cobond® 1000 from National Starch and Chemical Company and other aldehyde containing polymers such as those described in U.S. Pat. No. 6,224,714, issued on May 1, 2001, to Schroeder et al.; U.S. Pat. No. 6,274,667, issued on Aug. 14, 2001, to Shannon et al.; U.S. Pat. No. 6,287,418, issued on Sep. 11, 2001, to Schroeder et al.; and, U.S. Pat. No. 6,365,667, issued on Apr. 2, 2002, to Shannon et al., the disclosures of which are herein incorporated by reference to the extent they are non-contradictory herewith.

Permanent wet strength agents comprising cationic oligomeric or polymeric resins can be used in the present invention. Polyamide-polyamine-epichlorohydrin type resins also referred to as polyaminoamide-epichlorohydrin resins such as KYMENE 557H sold by Hercules, Inc., located at Wilmington, Del., are the most widely used permanent wet-strength agents and are suitable for use in the present invention. Such materials have been described in the following U.S. Pat. No. 3,700,623, issued on Oct. 24, 1972, to Keim; U.S. Pat. No. 3,772,076, issued on Nov. 13, 1973, to Keim; U.S. Pat. No. 3,855,158, issued on Dec. 17, 1974, to Petrovich et al.; U.S. Pat. No. 3,899,388, issued on Aug. 12, 1975, to Petrovich et al.; U.S. Pat. No. 4,129,528, issued on Dec. 12, 1978, to Petrovich et al.; U.S. Pat. No. 4,147,586, issued on Apr. 3, 1979, to Petrovich et al.; and, U.S. Pat. No. 4,222,921, issued on Sep. 16, 1980, to van Eenam. Other cationic resins include polyethylenimine resins and aminoplast resins obtained by reaction of formaldehyde with melamine or urea. It can be advantageous to use both permanent and temporary wet strength resins in the manufacture of tissue products.

In one embodiment, a relatively large amount of a wet strength agent is incorporated into the nonwoven material. The wet strength agent may also add to the dry strength of the product. In addition, wet strength agents aid in the chemical entangling of the fibers in the material to improve the retention of the conductive fibers. The amount of wet strength agent added to the nonwoven material can depend upon various different factors. In general, for instance, the wet strength agent can be added in an amount from about 1 kg/mton to about 12 kg/mton, such as from about 5 kg/mton to about 10 kg/mton. In certain embodiments, it may be desirable to add as much wet strength agent as possible. In these embodiments, for instance, the wet strength agent can be added in amounts greater than about 7 kg/mton, such as in amounts greater than about 8 kg/mton.

Dry strength agents are well known in the art and include but are not limited to modified starches and other polysaccharides such as cationic, amphoteric, and anionic starches and guar and locust bean gums, modified polyacrylamides, carboxymethylcellulose, sugars, polyvinyl alcohol, chitosans, and the like. Such dry strength agents are typically added to a fiber slurry prior to tissue sheet formation or as part of the creping package.

Additional types of chemicals that may be added to the nonwoven web include, but is not limited to, absorbency aids usually in the form of cationic, anionic, or non-ionic surfactants, humectants and plasticizers such as low molecular weight polyethylene glycols and polyhydroxy compounds such as glycerin and propylene glycol. Materials that supply skin health benefits such as mineral oil, aloe extract, vitamin E, silicone, lotions in general and the like may also be incorporated into the finished products.

In general, the products of the present disclosure can be used in conjunction with any known materials and chemicals that are not antagonistic to its intended use. Examples of such materials include but are not limited to baby powder, baking soda, chelating agents, zeolites, perfumes or other odor-masking agents, cyclodextrin compounds, oxidizers, and the like. Of particular advantage, when carbon fibers are used as the conductive fibers, the carbon fibers also serve as odor absorbents. Superabsorbent particles, synthetic fibers, or films may also be employed. Additional options include dyes, optical brighteners, humectants, emollients, and the like.

Nonwoven webs made in accordance with the present disclosure can include a single homogeneous layer of fibers or may include a stratified or layered construction. For instance, the nonwoven web ply may include two or three layers of fibers. Each layer may have a different fiber composition. The particular fibers contained in each layer generally depends upon the product being formed and the desired results. In one embodiment, for instance, a middle layer contains pulp fibers in combination with the conductive fibers. The outer layers, on the other hand, can contain only pulp fibers, such as softwood fibers and/or hardwood fibers.

In one embodiment, nonwoven webs made in accordance with the present disclosure are generally made according to a wetlaid process. In this embodiment, the fibers are combined with water to form an aqueous suspension and then deposited onto a porous forming surface where a wet web is formed. In one embodiment, an aqueous suspension containing the pulp fibers is first produced. The conductive fibers, such as the carbon fibers, are then injected into the aqueous suspension of pulp fibers prior to depositing the aqueous suspension onto the forming surface. For example, the conductive fibers can be injected into the aqueous suspension of pulp fibers in a headbox just prior to depositing the fibers onto the forming surface. The aqueous suspension of pulp fibers, for instance, may contain greater than 99% by weight water. For instance, in one embodiment, the aqueous suspension of pulp fibers contains the pulp fibers in an amount of less than 1% by weight, such as in an amount of about 0.5% by weight. The conductive fibers can then be injected into the aqueous suspension at a similar dilution. For instance, an aqueous suspension of carbon fibers containing carbon fibers in an amount of about 0.5% by weight may be injected into the aqueous suspension of pulp fibers.

Injecting the conductive fibers into an aqueous suspension of pulp fibers has been found to reduce the formation of flocks of the carbon fibers. It has been discovered that flocks have a greater tendency to form when the amount of time the fibers are mixed together increases. The creation of flocks, for instance, can produce weak spots in the resulting material and cause wet breaks when the nonwoven material is later processed.

For the most part, typical applications for both gas sensitive chemi-capacitive and chemi-resistive sensors are similar. That is, they are adapted to detect or quantify the presence of volatile agents inside a micro environment. Chemi-capacitive sensors, however, also can be use in so-called "remote query" applications, where one capacitive based sensor is connected to an Induction coil (L). The sensor construction is similar to that shown in FIG. 6, as described below. This L-C has a natural resonant frequency that shifts as "C" changes. This can be a queried by a secondary induction coil placed in near proximity to the sensor coil. As resonant frequency of the sensor coil changes, the corresponding resonant frequency of the secondary coil will change as well.

Section II

Chemi-Resistor

According to an embodiment, the gas sensors used can be configured as chemi-resistors. In general, a "chemiresistor" is a resistor whose electrical resistance changes upon exposure to molecules of one or more chemical species. Chemi-resistors comprise a chemi-resistive material disposed across or between at least a pair of spaced-apart electrodes. The chemi-resistive material comprises at least one electrically-conductive material (e.g., particles, fibers) that is sensitive to absorption or adsorption of a particular analyte (e.g., a volatile organic compound, water vapor, etc.). When the analyte absorbs or adsorbs into the polymeric material, the polymeric material swells. This swelling increases the spacing between adjacent electrically-conductive particles present in the chemi-resistor, which results in an increase in electrical resistance in the chemi-resistor. This change in resistance (or a corresponding change in another electrical property, such as conductance) can be measured and recorded, and used to signal a caregiver and/or a wearer of the absorbent article when an insult has occurred. Because this process is reversible (i.e., the analyte may desorb from the polymeric material, thus reducing the resistance of the chemi-resistor), the chemi-resistors may be used to detect multiple insults.

The chemi-resistors of the present disclosure are selected to be sensitive to absorption or adsorption of certain volatile organic compounds (VOCs) and, in particular, are selected to be sensitive to VOCs that are associated with a particular body waste or exudate, such as urine, feces, menstrual fluid, and/or blood. As used herein, the term "volatile organic compound" is meant to include both the organic and inorganic metabolic gases and compounds produced by microbes present in body wastes or exudates.

Particular VOCs may be associated with one or more types of body waste. VOCs commonly associated with urine include, for example, ammonia compounds (e.g, ammonia hydroxide), short chain ($C_1$-$C_2$) acids (e.g., acetic acid), medium length ($C_8$-$C_{10}$) aldehydes (e.g., nonanal), ketones (e.g., methyl ethyl ketone), cresol (e.g., methylphenol), dimethyl disulfide, trimethylamine, limonene (e.g., 4-isopropenyl-1-methylcyclohexane), acetic acid, methyl benzoate, benzamide, benzaldehyde, and triethylamine, among others. VOCs commonly associated with feces include, for example, skatole (e.g., 3-methyl-1H-indole, 3-methylindole, etc.), mercaptans (e.g., 2-mercaptoethanol), hydrogensulfide, short chain fatty acids (e.g., myristic acid), methanethiol (e.g., 2-mercaptoethanol), and dimethylsulfide, among others. VOCs commonly associated with menstrual fluid include, for example, trimethylamine, among others.

The specificity of a chemi-resistor for a particular VOC depends on the polymeric material used in the chemi-resistor. In general, different polymers will absorb or adsorb VOCs with varying degrees of specificity. Suitable polymeric materials are typically selected by first determining the chemical properties of the VOC to be detected, e.g., whether the VOC is hydrophilic or hydrophobic, the polarity of the VOC, functional groups of the VOC, etc. Preferably, the chemical properties of the polymeric material selected are similar to the properties of the VOC to be detected.

In one embodiment, the polymeric material can be selected on the basis of its solubility parameter, $\Delta$, which is preferably about the same as the solubility parameter of the VOC to be sorbed into the polymeric material. When the solubility parameters, $\Delta$, of the polymer material and the VOC are about the same, there will be a substantial interaction between the molecules of the polymeric material and the VOC, thereby leading to a substantial sorption of the VOC into the polymeric material. Solubility parameters, $\Delta$, for various polymers and VOCs can be determined from simple experiments, can be readily computed, or can be determined from tables in chemical reference books (see also U.S. Pat. No. 6,902,701, incorporated herein by reference).

The suitability of a particular polymer for detecting a VOC can also be easily and readily determined by one skilled in the art experimentally based in part on the disclosure herein. For example, once a polymer having chemical properties similar to those of the VOC to be detected has been selected, a chemi-resistor comprising the polymer may then be tested (e.g., by using a method such as the one described in the examples herein) to determine if there is a resistance change when the chemi-resistor is exposed to the VOC. Polymers that result in a large resistance change are preferably used in the chemi-resistor.

The change in resistance (or other electrical property as noted above) of the chemi-resistor in the presence of a target VOC is partially dependant on the concentration of the VOC. For example, resistance of the chemi-resistor will generally increase when exposed to increasing concentrations of the target VOC. An example of this is illustrated in FIG. 13, which shows the relationship between concentration of the VOC dimethyldisulfide and the resistance of a chemi-resistor comprising poly(ethylene-vinyl acetate) (PEVA). It is generally preferred that a chemi-resistor of the present disclosure be capable of detecting the target VOC (e.g., exhibit an increase in resistance in the presence of the target VOC or exhibit a change in another electrical property, such as conductivity) at a target VOC concentration of at least about 1 ppm.

Particular polymeric materials that can be used to form the chemi-resistors used in the present disclosure include polyepichlorohydrin (PECH), poly(N-vinyl pyrrolidone) (PVNP), polyisobutylene (PIB), poly(ethylene-vinyl acetate) (PEVA), poly(vinyl alcohol) (PVA), ethyl cellulose (EC), and poly(diphenoxyphosphazine) (PDPP), among others. Preferably, the polymeric material is selected from the group consisting of PECH, PVNP, PIB, and PEVA.

In addition to sorbing particular VOCs, certain polymers may also be sensitive to water vapor. Consequently, water vapor (e.g., from perspiration of the wearer or from the external environment) may also be sorbed by the polymeric material and affect the resistance of the chemi-resistor. As discussed above with respect to VOCs, the sensitivity of a polymeric material to water vapor will depend on the chemical properties of the polymeric material. For example, chemiresistors comprising PNVP are sensitive to water vapor (i.e., have a change in resistance when exposed to saturated water vapor), while chemi-resistors comprising PEVA, PIB, and PECH show little resistance change when exposed to saturated water vapor. By incorporating a chemi-resistor with sensitivity to water vapor into an absorbent article, the comfort level of the wearer of the absorbent article may also be monitored.

As discussed above a polymeric material can be selected to provide a high sensitivity or selectivity for detection of a particular VOC by matching the chemical properties of the polymeric material with those of the VOC to be detected. Thus, in one embodiment, the absorbent articles of the present disclosure may comprise a single chemi-resistor that is sensitive to a particular type of VOC. For example, PECH is particularly sensitive to aromatics and chlorinated hydrocarbons, as well as benzaldehydes. PVNP, a polar compound, is sensitive to polar VOCs, such as trimethylamine, benzaldehyde, ammonia, mercaptans, and water vapor. PIB and PEVA are hydrophobic and are sensitive to hydrophobic VOCs, such as limonene and benzaldehydes. PIB is also sensitive to nonpolar VOCs.

In addition, the absorbent articles of the present disclosure may comprise a single chemiresistor that is sensitive to the presence of more than one type of VOC. For example, a particular polymeric material may be sensitive to a class of VOCs that share similar functionality or chemical subgroups within their structure. A chemiresistor comprising such a polymer may show a change in resistance when exposed to any one of a number of VOCs in the class. However, the degree of change will typically be different for each individual VOC. For example, a polymer will typically be more responsive to one particular VOC than other VOCs, even if showing some change in resistance for more than one VOC in the class. Consequently, if multiple types of VOCs are to be detected, it is generally preferable to use a different chemiresistor for each individual VOC.

In another embodiment, the absorbent articles of the present disclosure may comprise more than one chemiresistor. In this embodiment, the chemi-resistors may each be sensitive to different VOCs or, alternately, some or all of the chemi-resistors may be sensitive to the same VOC. For example, the absorbent article may comprise multiple chemi-resistors, some or all of which are sensitive to the same VOC, wherein the chemi-resistors are located on different areas of the absorbent article, as discussed below. In another example, the absorbent article may comprise two or more chemi-resistors, with some or all of the chemi-resistors being sensitive to VOCs associated with different types of insults. In this instance, the chemi-resistors may be used to differentiate between different types of insults based on the VOC detected.

In addition to the polymeric material, the chemi-resistive material further comprises a plurality of electrically-conductive particles. The electrically-conductive particles provide multiple conduction pathways for an electrical current to flow when a voltage is applied between the spaced-apart electrodes. Typically the electrically-conductive particles are uniformly distributed throughout the entire volume of the chemiresistive material.

Figure 3:
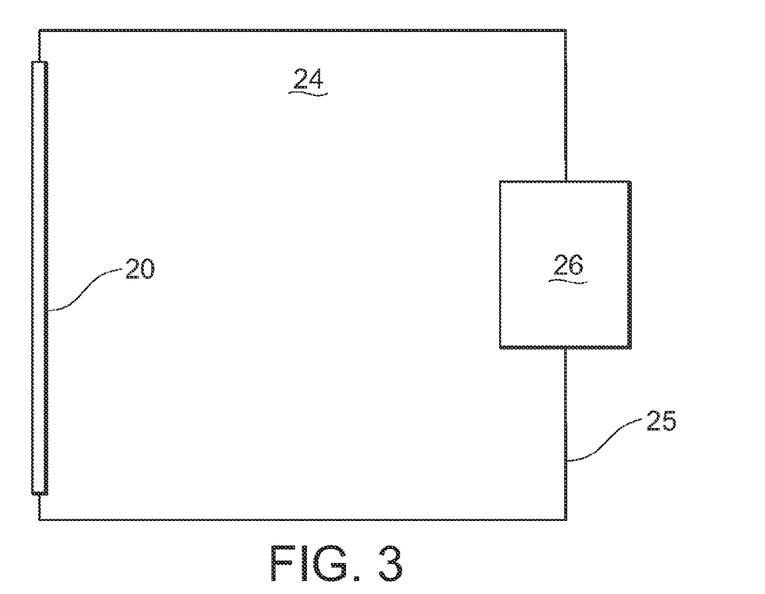
FIG. 3 is a schematic representation of a chemi-resistive gas sensor 20 according to the present invention, attached to a detector or processor 26 by a circuit 24.

When configured for a chemi-resistive sensor, a nonwoven web substrate by itself is sufficient, such as illustrated in FIG. 3, which shows an arrangement of the present nonwoven-based gas chemisensor as a resistive sensor 20 in a circuit loop 24 in communication with a processor or reader mechanism 26. The sensor and processor may be either physically connected by a wire 25, or they may be wireless.

To construct a chemi-resistive sensor, one could use conventional nonwovens fabrication processes such as either a wet-laid (e.g., paper making process) or dry-laid process (e.g., airlaid or coform fabrications). The nonwoven material is typically made from a matrix of a majority of inert thermoplastic filaments or fibers (e.g., polypropylene, polyethylene, polyesters), and pulp or cellulose-based fibers, or staple fibers, or a mixed combination thereof. Within or over this basic fiber matrix, at least a gas responsive fiber and a conductive fiber are interwoven or associated otherwise by mixing together with each other to form an electrically conductive nonwoven material. The active gas-sensitive fibers made from various gas-absorbing polymers are interspersed along with electrically conductive fibers. As the gas-sensitive fibers absorb a VOC, the dimensions of the fiber will change, and depending on the particular VOC, a change in the dimensions of the gas-sensitive fibers will disrupt the network of conductive fibers, and can cause the resistance to electrons to increase as a function of the amount of VOC absorbed to the nonwoven material.

According to a fabrication process, in general, the conductive nonwoven is cut to an appropriate size to be used as a sensor. Depending on the intended application, typically the nonwoven substrate of the sensor can have dimensions between about 1 cm or 2 cm, or 5-8 cm (~1-3 inches), such as for use in respirators or masks, or up to about 25-80 cm (1-3 feet) for air filters, or they can be larger for other uses or configurations. According to an embodiment, an alcohol gas sensor, for example, can be made by using 3 mm chopped polyvinyl alcohol (PVOH) fibers and 3 mm chopped carbon fibers. A 16 gsm sheet with 6% carbon fiber was made and used as a chemi-resistor sensor. The result of the alcohol absorbance and impact on the resistance is shown the experimental section below.

For chemiresistor construction, a 16 gsm sheet (PVOH and 6% carbon fiber) was made and used as a chemiresistor sensor. The result is shown in the attachment. For chemicapacitor construction, a 32 gsm alcohol sensing layer was first made using 3 mm chopped polyvinyl alcohol (PVOH) fiber and cellulose fiber (LL19) at 50/50 ratio. A chemiresistor sensor was constructed by mating a sheet of PVOH/cellulose between two layers of 37 gsm conductive paper (10% carbon fiber).

The chemiresistive material comprises from about 3 wt. % to about 60 wt. %, typically from about 5 or 6 wt. % to about 40 or 45 wt. % of an electrically-conductive material. More typically the electrically-conductive material is in an amount between about 7 or 8 wt. % and about 30 or 35 wt. %, preferably between about 9 or 10 wt. % to about 27 or 30 wt. %. In general, any electrically-conductive material may be used. Suitable electrically-conductive materials are known in the art and include, for example, carbon fiber, metal coated fiber materials, and the like. Preferably, the electrically-conductive material comprises carbon fibers. The exact size of the electrically-conductive fibers is not critical, but generally is from about 1 mm or 2 mm to about 12 mm or 15 mm in length.

Section III

Chemi-Capacitor

Figure 4:
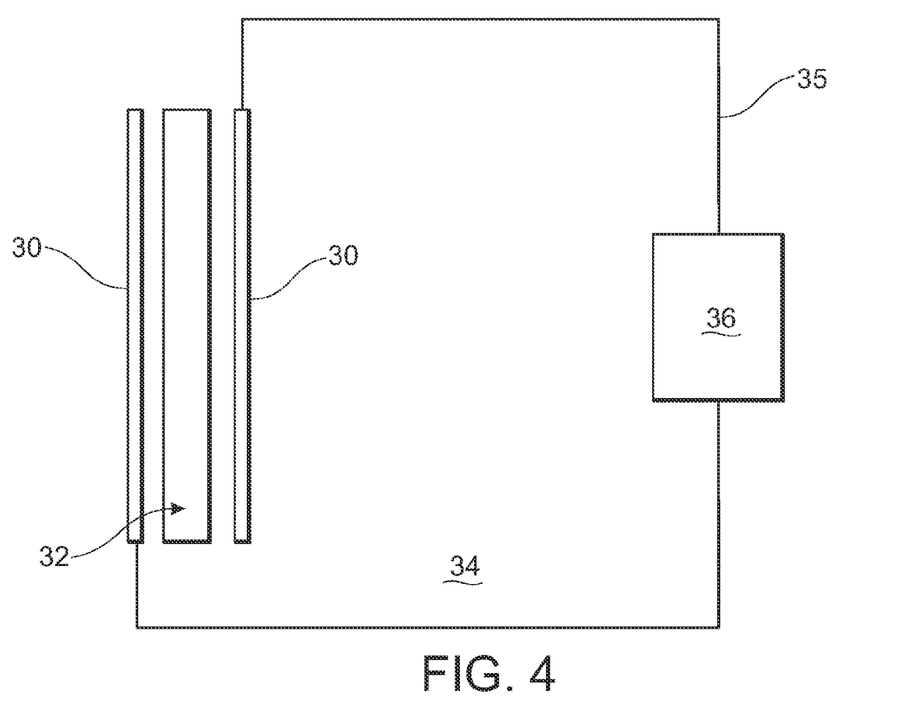
FIG. 4 is a schematic representation of a chemi-capacitive gas sensor according to the present invention with a chemi-sensitive polymer 32 situated between two conductive nonwoven-based material substrates 30, in communication with a detector or processor 36 by a circuit 34.

According to another embodiment, the gas sensors can be chemi-capacitors. When configured for a chemi-capacitive construction, a non-conductive gas sensing layer is situated between two conductive nonwoven web layers of the present invention, such as illustrated in FIG. 4, to form a capacitor. FIG. 4 shows an arrangement of the present nonwoven-based gas chemisensor as a capacitive sensor, comprising conductive plates 30 and dielectric layer 32. The chemi-sensitive dielectric polymer 32 is sandwiched between two conductive nonwoven layers 30, which can be connected to or associated with a circuit loop 34 and in communication with a data processor, reader, detection or electronic output device or other associated electronic mechanism or hardware 36. Like with the chemi-resistive format, the sensor can be either physically connected by a wire 35, or they can be wireless.

Although the literature describes certain kinds of chemi-capacitive gas sensors, those sensor devices are very different in construction and method of operation from the present invention. The literature describes a type of gas sensor that is constructed using micro-machined, metallic, parallel-plate capacitors. One of the plates has an array of holes to allow a gas of interest to interact with the dielectric material, which is sandwiched between the parallel-plates. An important difference between the present invention and these other kinds of gas sensors is in the construction of the capacitor.

In contrast, an advantage of conductive nonwoven-based layers is their relative porosity. The nonwoven substrate should have a gas permeability of greater than 200 sq. microns of air. Typically, the permeability is in a range from about 220 sq. microns to about 600 sq. microns, more typically between about 230 or 250 sq. microns up to about 520 or 550 sq. microns, or to about 430 or 450 sq. microns. The present gas sensors are thin and flexible and do not require purposeful perforations (holes) to allow gases to ingress and interact with the detection material. Rather, the permeable nature of a nonwoven-based web material permits the gas to freely interact with the gas-sensitive fibers. A gas exchange or flow from the outside environment into the sensor is relatively unrestricted, which permits VOCs to go through the fiber web of the nonwoven material and absorb on the sensing layer. Once the VOCs absorb to the sensing layer, the dielectric properties of the sensing layer changed. These changes triggered a change in a capacitance value of the sensor. According to an embodiment, the non-conductive sensing layer is sandwiched between two layers of conductive paper. The constructed capacitor is cut to an appropriate size to be used as a gas sensor. For instance, the nonwoven can be made into a substrate that has, for example, dimensions that can produce an area of about 0.125 $cm^2$ or 0.5 $cm^2$, or 1 $cm^2$, up to about 20 $cm^2$, 30 $cm^2$, 40 $cm^2$, or 50 $cm^2$ or greater, as with the chemi-resistive format. Typically, the dimensions can produce an area of between about 1 or 1.25 $cm^2$ to about 12 $cm^2$ or 15 $cm^2$; or more typically between about 2, 3 or 4 $cm^2$ to about 7, 8 or 10 $cm^2$, inclusive of all values in such ranges.

Similar to the chemi-resistive format, at least a gas responsive fiber is used to form a sensing nonwoven material, which could be done using either a wet-laid or dry-laid process as described above.

As an example, an alcohol sensing layer is made in the lab by using 3 mm chopped polyvinyl alcohol (PVOH) fiber and cellulose fiber (LL19) at 50/50 ratio. A chemi-capacitor sensor was constructed by forming a 32 gsm sheet of PVOH/cellulose and sandwiched between two layers of 37 gsm conductive paper (10% carbon fiber). The results are summarized in the empirical section below.

Section IV

System Block Diagram and Hardware Design of Electronic Detection Methods of Nonwoven Gas Sensor There are several methods of measuring change in capacitance. The present invention envisions that one can construct nonwoven-based gas sensors according to two general methods; namely, capacitive based sensors and resistive based sensors. Each approach can employ different variations in the way the detection circuits are arranged. These variations in construction are described herein.

A. Capacitance-Based Nonwoven Gas Sensor

For a capacitance-based nonwoven gas sensor, the sensor can be constructed by sandwiching a PVA based coform material between two layers conductive nonwoven material. This forms a typical parallel plate capacitor-based sensor. In presence of volatiles like alcohol vapor, the inner nonwoven layer expands causing the capacitance of the parallel plate capacitor to change, which can be detected by the following detection circuit configurations.

Arrangement 1: Charge Time Measurement Unit Method

Figure 5:
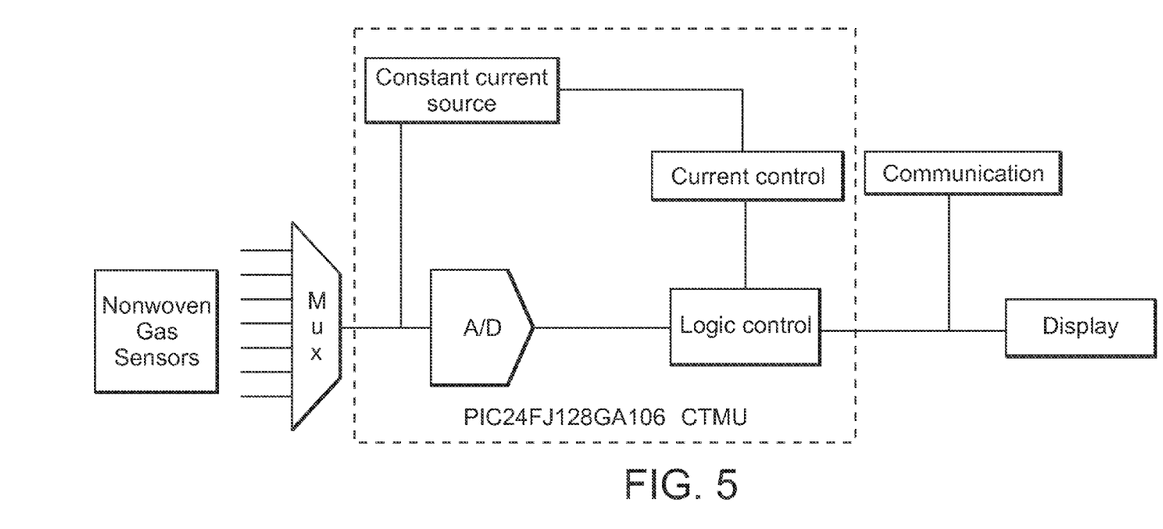
FIG. 5 is a block diagram showing a circuit arrangement with a charge time measurement unit (CTMU) for measuring capacitance according to an embodiment of the present invention.

The system design for this configuration includes a microcontroller, such as made by Microchip Technologies Inc. (part number (PIC24FJ128GA106)), which has a dedicated charge time measurement unit (CTMU). The CTMU is a module add-on to the microcontroller which can be employed directly to detect changes in capacitance. With such a system design, an array of nonwoven-based capacitor gas sensors were attached to the A/D inputs of the microcontroller (Microchip PIC 24FJ series) and used to compute the changes in capacitance as the dielectric changes in presence of alcohol vapor. FIG. 5, illustrates the circuit system. This capacitance measuring circuit is similar to one such as disclosed in U.S. patent application Ser. No. 12/648,645, the contents of which are incorporated herein.

Arrangement 2: Tuned Resonator Circuit

Figure 6:
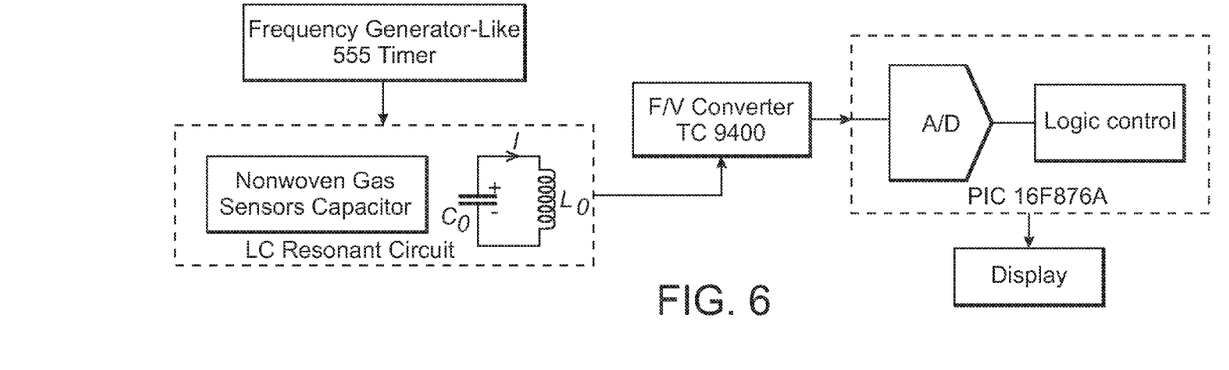
FIG. 6 is a block diagram of an alternative LC resonator circuit configuration for measuring capacitance.

Alternatively, one may detect changes in the resonant frequency of a tuned circuit or LC circuit, with an inductor, represented by the letter L, and a capacitor, represented by the letter C. As the capacitance value of the resonator circuit changes the frequency of the oscillating frequency of the resonator changes, this can be detected by a Frequency to Voltage (F/V) converting chip like TC 9400 made by Microchip Technologies Inc. FIG. 6 shows the block diagram of such a system. The voltage generated by F/V can be fed directly into a microcontroller like PIC 16F876A as made by Microchip Technologies where the analog voltage signal is digitized and logic to compute the quantity of vapor detected is computed.

B. Resistive-Based Nonwoven Gas Sensor

As described above, the gas sensor can be constructed by incorporating gas sensing polymers inside a conductive nonwoven material, such as conductive paper. As the material is exposed to volatile gases or vapors the sensitive polymer expands, thereby changing the resistance of the conductive material. Several circuit arrangements exist for measuring changes in resistance. For purposes of illustration, two examples of such system configurations are discussed below.

Arrangement 1: Voltage Divider Circuit

Figure 7:
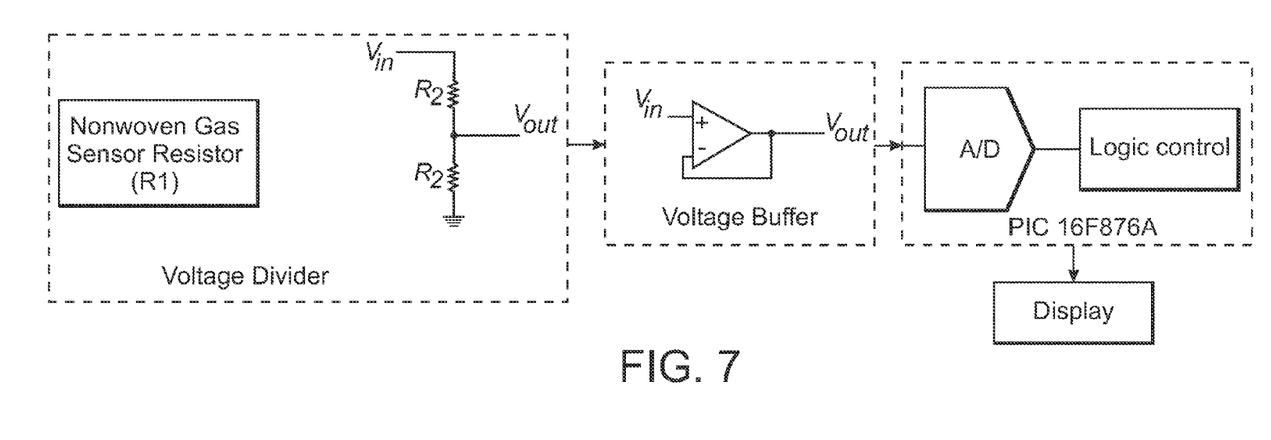
FIG. 7 is a block diagram showing a circuit arrangement with a voltage divider for measuring resistance according to an embodiment of the present invention.

A voltage divider circuit, such as depicted in accompanying FIG. 7, produces a voltage that is a fraction of the input voltage and is dependent on the two resistors chosen as a divider. As soon the nonwoven gas sensor comes in contact with the volatile gas or vapor, the resistance of the gas sensor changes, which also changes the output voltage. This output voltage is fed into a buffer amplifier, like a LM241 as made by National Semiconductors, to help provide a high impedance input into an A/D convertor. The voltage from the buffer amplifier can be fed directly into a microcontroller like PIC 16F876A as made by Microchip Technologies Inc., where the analog voltage signal is digitized and logic to quantify the amount of volatile is present is computed.

Arrangement 2: Wheatstone Bridge Circuit

Figure 8:
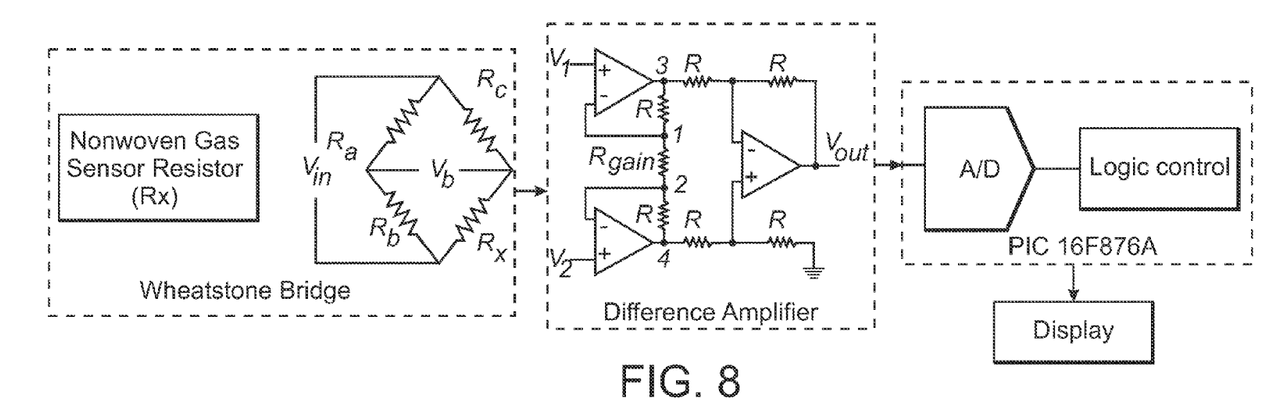
FIG. 8 is a block diagram of an alternative Wheatstone Bridge circuit configuration for measuring resistance.

A wheatstone bridge circuit, such as shown in FIG. 8, is used to measure an unknown electrical resistance by balancing two legs of a bridge circuit, one leg of which includes the unknown component (Rx). The voltage difference between the two legs of the bridge circuit (Vb) can be amplified using a difference amplifier circuit shown below. This voltage can be fed directly into a microcontroller like PIC 16F876A as made by Microchip Inc. where the Analog voltage signal is digitized and logic to quantify the amount of volatile is present is computed.

Section V

Empirical Examples

The following examples further demonstrate the gas sensors made in accordance with the present invention.

Example 1

A chemi-resistive material was made using a paper handsheet former. The carbon fiber used was TENAX 150 fibers obtained from Toho Tenax having a cut length of 3 mm and polyvinyl alcohol fiber used was VPW 101 from Kuraray having a cut length of 3 mm. An amount of 0.045 grams of carbon fiber and 0.7 gram of polyvinyl alcohol were dispersed with water at approximately 40° C. to a consistency of approximately 1.2 percent solids for 5 minutes in a British Pulp Disintegrator, available from Lorentzen and Wettre, Atlanta, Ga. The slurry was then diluted to 0.3 consistency and formed into a handsheet on a square (9×9 inches) Valley Handsheet Mold, available from Voith Inc., Appleton, Wis. The handsheet was couched of the mold by hand using a papertowel sheet and pressed wire-side up at 100 pounds per square inch for 1 minute. Next the handsheet was placed in between two release paper and dried wire-side up for 2 minutes using a Valley Steam Hotplate, available from Voith Inc., Appleton, Wis., with a weighted canvas cover having a lead filled brass tube weighing 4.75 pounds to maintain tension.

Figure 9:
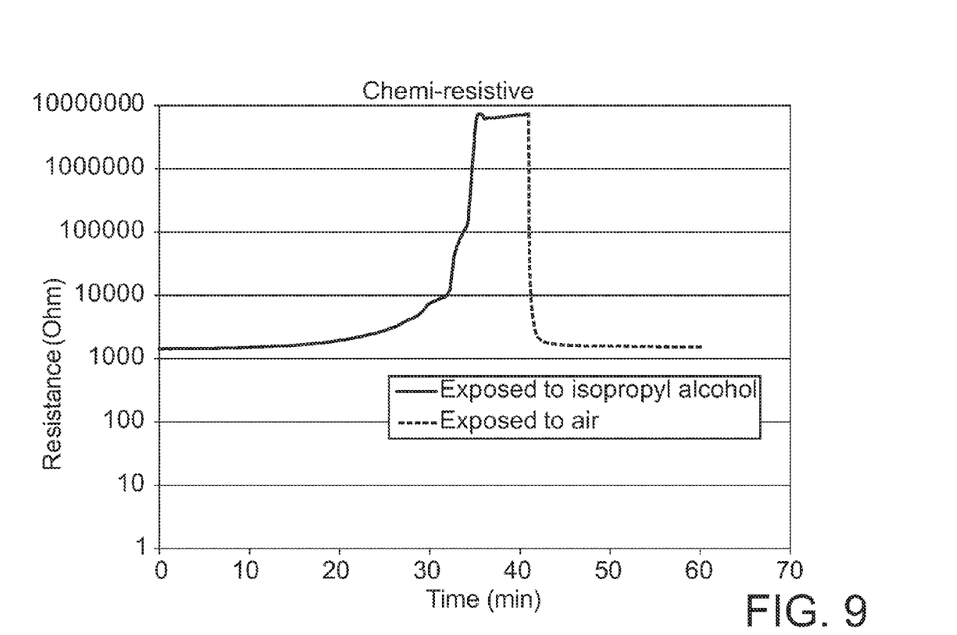
FIG. 9 is a graph showing the efficacy of the present nonwoven-based gas chemisensor in resistive detection of isopropyl alcohol vapor.

A 2"×0.5" strip was cut from the resulting sheet and placed over the top of a 100 ml glass beaker containing about 20 ml of isopropyl alcohol. The strip was connected to Agilent 34401A Digital Multimeter, available from Agilent Technologies, Inc., to collect resistance data as a function of time. The beaker and the strip are covered with a plastic wrap. The result was shown in accompanying FIG. 9. In the closed system, when exposed to isopropyl alcohol vapor, the resistance of the sensor builds up from about 1,000 Ohms to a heightened level plateau, and remains near the plateau of about 10,000,000 Ohms until exposed to ambient air, at which point the resistance returns to original levels.

Example 2

A chemi-capacitive material was made using a paper handsheet former.

Outer Layers:

The outer layers of the sensor is constructed from a conductive paper that was made on a paper machine as described in U.S. patent application Ser. No. 11/888,334, and Ser. No. 12/130,573, the contents of which are incorporated herein, using TENAX 150 carbon fiber (obtained from Toho Tenax) having a cut length of 3 mm and LL19 wood pulp fiber used (from Terrace Bay Pulp Inc). The conductive paper had a basis weight of 37 gram per square meter, and it contained 10% carbon fibers.

Middle Layer:

The middle layer of the sensor is made from wood pulp fiber (northern bleached softwood kraft fibers LL19, available from Terrace Bay Pulp Inc.), and polyvinyl alcohol fiber (VPW 101 from Kuraray) that has a cut length of 3 mm. About 0.86 grams of wood pulp fiber and 0.86 gram of polyvinyl alcohol were dispersed with water at approximately 40° C. to a consistency of approximately 1.2 percent solids for 5 minutes in a British Pulp Disintegrator, available from Lorentzen and Wettre, Atlanta, Ga. The slurry was then diluted to 0.3 consistency and formed into a handsheet on a square (9×9 inches) Valley Handsheet Mold, available from Voith Inc., Appleton, Wis. The handsheet was removed of the mold by hand and two conductive paper sheets were placed on both sides of the handsheet. The combined handsheet pressed at 100 pounds per square inch for 1 minute. Next the combined handsheet was dried for 2 minutes using a Valley Steam Hotplate, available from Voith Inc., Appleton, Wis., with a weighted canvas cover having a lead filled brass tube weighing 4.75 pounds to maintain tension.

Figure 10:
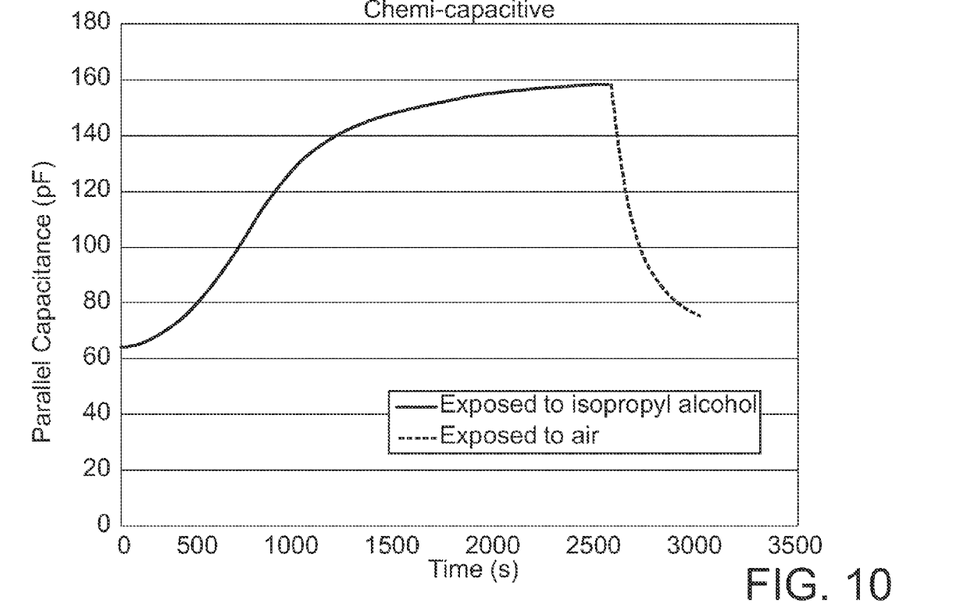
FIG. 10 is a graph showing the efficacy of the present nonwoven-based gas chemisensor in capacitive detection of isopropyl alcohol vapor.

A 2.5 cm×1.5 cm strip was cut from the resulting sheet. Copper foil tape 1181, available from 3M, were cut into 0.5 cm×0.5 cm strips. A copper wire was soldered to each copper foil tape strip to make an electrical connection. The copper foil tape strips with copper wire were attached to each side of the conductive nonwoven strip. The conductive nonwoven strip was placed over the top of a 100 ml glass beaker containing about 50 ml of isopropyl alcohol. The two wires from the strip are connected to a 889A Bench LCR/ESR meter, available from B&K Precision Corp. to collect capacitance data as a function of time. The beaker and the strip are covered with a plastic wrap. The result was shown in accompanying FIG. 10. In the closed system, the capacitive function quickly rises from about 60 pF to almost 160 pF when exposed to the isopropyl alcohol vapor. When exposed to outside air, the capacitive function quickly drops to below 80 pF.

The present invention has been described generally and by way of examples. Persons skilled in the art will understand that the invention is not necessarily limited to the embodiments specifically disclosed, and that modifications and variations can be made without departing from the scope of the invention as defined in the following claims.

We claim:

1. A chemical gas sensor comprising:
a flexible, gas-permeable, nonwoven web-based material substrate having a matrix that is composed of a plurality of inert thermoplastic, pulp, cellulose or staple fibers as either a major or minor portion, with a plurality of gas-sensitive fibers formed from a polymer that can absorb volatile organic compounds (VOC), and a plurality of electrically conductive fibers;
said gas-sensitive fibers are intermixed with and associated spatially among a network of adjacent electrically conductive fibers, such that a change in physical morphology of said gas-sensitive fibers as a result of interacting with volatile organic compounds, causes a change in physical or dielectric properties that disrupts said network of adjacent electrically conductive fibers;
said nonwoven-based material having a gas permeability of greater than 200 sq. microns of air;
wherein said gas-sensitive fibers are formed from polyethylene-vinyl acetate (PEVA).

2. The chemical gas sensor according to claim 1, wherein said flexible nonwoven matrix is a stand-alone sheet for a resistive sensor.

3. The chemical gas sensor according to claim 1, wherein said flexible nonwoven matrix is situated between two conductive layers to form a capacitor.

4. The chemical gas sensor according to claim 3, wherein said conductive layers are sheets of conductive paper comprising carbon fibers.

5. The chemical gas sensor according to claim 1, wherein said VOCs include aromatic and chlorinated hydrocarbons, triethylamine, benzaldehyde, ammonia, marcaptans, dimethyl disulfide, alcohol vapor, and water vapor.

6. The chemical gas sensor according to claim 1, wherein said gas-sensitive fibers comprise from about 5 wt. % to about 95 wt. % of said nonwoven matrix.

7. The chemical gas sensor according to claim 1, wherein said electrically conductive fibers comprise from about 5 wt. % to about 80 wt. % of said entire nonwoven matrix.

8. The chemical gas sensor according to claim 1, wherein said flexible nonwoven matrix is sensitive to a relative resistivity change between about 1000 Ohms to about 10,000,000 Ohms.

9. The chemical gas sensor according to claim 1, wherein said flexible nonwoven matrix is sensitive to a change of at least about 10-100 pF, when arranged as a capacitive chemisensor.

* * * * *